United States Patent [19]

Paikoff et al.

[11] Patent Number: 4,523,679
[45] Date of Patent: Jun. 18, 1985

[54] PRE-STERILIZED MEDICAL PROCEDURE KIT PACKAGES

[75] Inventors: Myron Paikoff, Colonie, N.Y.; Robert W. Hain, Scotch Plains; Frederick B. Hadtke, New Providence, both of N.J.

[73] Assignee: Sterling Drug Inc., New York, N.Y.

[21] Appl. No.: 586,159

[22] Filed: Mar. 5, 1984

[51] Int. Cl.³ .......................... A61B 19/02; B65D 1/34
[52] U.S. Cl. ..................................... 206/370; 206/363; 206/438; 206/439; 206/570; 422/34
[58] Field of Search ............... 206/438, 440, 207, 210, 206/363, 367, 370, 484.1, 484.2, 570, 571, 572; 422/34, 300, 302

[56] References Cited

U.S. PATENT DOCUMENTS

| 659,058 | 10/1900 | Edlen | 206/572 |
|---|---|---|---|
| 2,947,415 | 8/1960 | Garth | 206/364 |
| 3,770,119 | 11/1973 | Hultberg et al. | 206/439 |
| 3,801,278 | 4/1974 | Wagner | 422/300 |
| 3,815,315 | 6/1974 | Glick | 422/34 |
| 3,851,645 | 12/1974 | Villari | 206/571 |
| 3,926,309 | 8/1973 | Center | 206/364 |
| 3,954,174 | 5/1976 | Kraus | 206/572 |
| 3,967,728 | 7/1976 | Gordon et al. | 206/364 |
| 4,085,845 | 4/1978 | Perfert | 206/363 |
| 4,128,173 | 12/1978 | Lazarus et al. | 206/570 |
| 4,149,635 | 4/1979 | Stevens | 206/370 |
| 4,153,160 | 5/1979 | Leigh | 206/370 |
| 4,405,047 | 9/1983 | Barba | 206/570 |
| 4,444,310 | 4/1984 | Odell | 206/526 |

FOREIGN PATENT DOCUMENTS

WO81/01545 6/1981 PCT Int'l Appl. ................. 206/572

Primary Examiner—Joseph Man-Fu Moy
Assistant Examiner—Brenda J. Ehrhardt
Attorney, Agent, or Firm—William G. Webb; B. Woodrow Wyatt; Paul E. Dupont

[57] ABSTRACT

This invention provides medical procedure packages comprising a pre-sterilized kit within an outer package wrap, the packages being so designed that all components of the package are sterilized using sterilization methods which are compatible with the chemical compositions of the components and their stability to such sterilization methods, and wherein the internal sterility of the package is maintained from final package sealing until the package is delivered to a sterile operating room environment.

8 Claims, 6 Drawing Figures

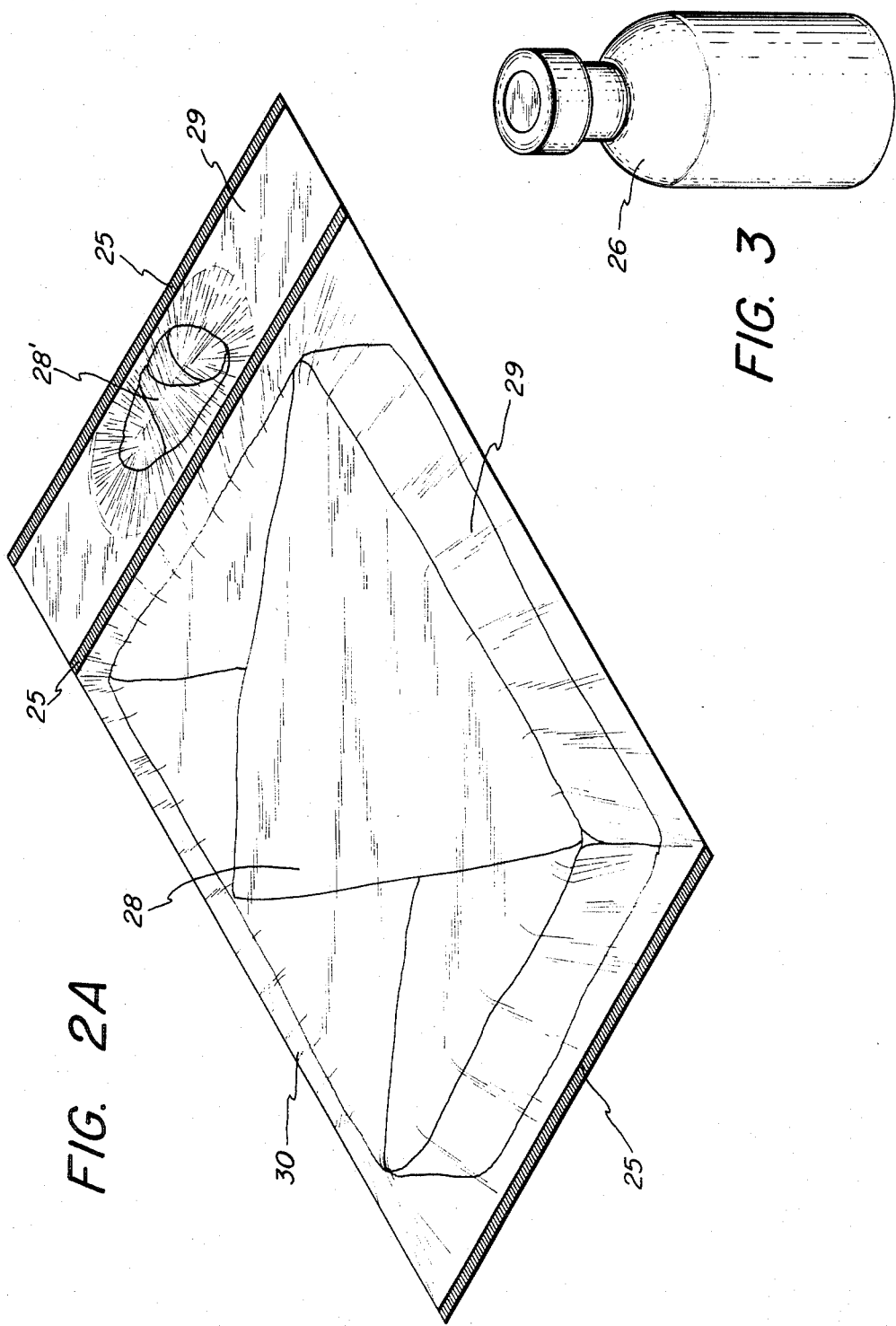

PRE-STERILIZED MEDICAL PROCEDURE KIT PACKAGES

RELATED APPLICATIONS

Paikoff Application Ser. No. 586,362, filed of even date herewith, discloses and claims a unitary, two-compartment medical procedure package kit containing, in one compartment thereof, certain medical procedure components and, in the other compartment, a sealed ethylene oxide impermeable container having therein a medicament containing vial. All the elements of the kit, except the medicament containing vial, are compatible with, and are sterilized by, ethylene oxide, while the vial is compatible with, and is separately sterilized by, heat. All the elements of the kit, including the heat sterilized vial within the sealed container, are combined and the entire kit sterilized by ethylene oxide before final packaging in a package whose interior is completely sterile and can be so-maintained until utlimate use of the package contents.

BACKGROUND

This invention relates to the field of sterile packaging of components to be used in certain medical operative procedures. More specifically, the invention relates to the packaging, in a single outer package, of various components used in such procedures where, because of the chemical nature of certain portions of some of the components, particular sterilization methods must be used with some of the components, while other different sterilization methods must be used with the others.

While the concept here-involved can be applied to the packaging of any medical procedure package requiring the inclusion of any medicament-containing vial which is conventionally sealed with a rubber closure plug or diaphragm, the packages provided by the present invention have particular use in X-ray radiographic procedures, such as myelographic procedures, in which a radiopaque contrast agent is injected into the spinal arachnoid space so as to provide X-ray visualization of the spinal chord. In such procedures, the skin area of the patient's spine where the injection is to be made is sterilized using appropriate sponge scrubbers and antibacterial agents. Then using a hypodermic syringe and a vial of local anesthetic, the area around the injection site is anesthetized. A spinal puncture needle is then inserted into the arachnoid space, and, if desired, samples of cerebro spinal fluid (CSF) are withdrawn by attachment of a cannula fitted with a male tapered joint on one end for attachment of the cannula to the puncture needle and a female tapered joint on the other end for attachment of the cannula to a hypodermic syringe, the samples being collected in small graduated sample tubes. The radiopaque solution is then withdrawn from a vial containing the same, conventionally sealed with a rubber plug, by puncturing the plug with a separate hypodermic needle and aspirating the solution into a syringe. The syringe is then disconnected from the aspirating needle, attached either directly to the puncture needle in the patient's spine or to the cannula attached to the needle, and the radiopaque medium is then injected into the arachnoid space. When the examination is complete, the puncture needle is withdrawn, leaving the radiopaque medium in place to be metabolized by the body, or, alternatively, the medium is removed by aspiration and then the puncture needle is withdrawn.

It will be clear from the above description that each of the various essential medical procedures components used in the myelographic procedure, including sponge scrubbers, local anesthetic syringe and vial, puncture needles with associated needle sheaths and closure caps, cannulas and associated closure caps, sample tubes, contrast agent vial and injection syringe, as well as miscellaneous items such as drapes to cover the patient and gauze pads for blotting fluids around the injection site during the procedure, must all be pre-sterilized before or during packaging and, most importantly, must be maintained in a sterile condition until used. The conventional approach to the problem of ensuring sterility in each of the components, some of which are typically made of plastic materials, has been to provide all the components, except the vial of contrast agent, in one package unit, such as a plastic tray typically made of polystyrene foam or thermo-formed polystyrene, the vial of contrast agent being supplied in a separate package. This separation of the vial of contrast agent from the remainder of the package contents in necessary, because the components stored and shipped in the plastic trays cannot be heat sterilized due to the instability of the plastics to heat. Thus the trays and their associated essential medial procedure components can only be sterilized by ethylene oxide gas. On the other hand, the vial of contrast agent, which, as stated, is conventionally sealed with a pierceable rubber plug, cannot be sterilized by ethylene oxide because of the known destructive effect the latter has on rubber. Thus the contrast agent vial can only be heat sterilized. The present invention provides a unique means for maintaining complete sterility of all the components used in the procedure while combining all the components, including the contrast agent vial, into a single package unit.

INFORMATION DISCLOSURE STATEMENT

Garth U.S. Pat. No. 2,947,415 discloses a plastic, heat-sealed package for holding medical and surgical items constructed of two layers of plastic, one of polyethylene, which is ethylene oxide permeable, and the other of Mylar, which the patentee states is gas impermeable. The packages are sterilized with ethylene oxide after sealing and packaging.

Hultberg et al. U.S. Pat. No. 3,770,119 discloses a sterile prepackaged tray containing pre-sterilized medical and surgical items needed to perform simple medical and surgical procedures such as liver biopsy or spinal anesthesia. The package comprises a tray, having compartments therein for holding medical and surgical items, and a drape sealed to the interior of the tray. When packaged for shipment, the drape is folded inside the tray, thus covering the tray contents. The entire assembly is then sealed with a gas-permeable, contamination-impermeable peelable sheet 14, sterilized with ethylene oxide or the like and then sealed. In use, the peelable sheet is removed, and the sterile drape is unfolded to provide a sterile field and to provide access to the tray and its contents.

Center U.S. Pat. No. 3,926,309 discloses a two-layer sterile package for two different articles. The package is so constructed that sequential access to the articles is provided without the necessity of disturbing the sterility of the second article when the first is removed. The first layer is a polyethylene envelope formed by folding the sides of a polyethylene sheet towards one another, leaving a space 16 between the edges thus forming a tube which is open along its side and at both ends, and then heat sealing the ends of the tube. The second layer is formed by heat sealing a gas-permeable, bacteria-impermeable paper over the first. The entire package is then gas sterilized and vacuum purged prior to shipment.

Gordon et al. U.S. Pat. No. 3,967,728 discloses a tandem type pouch package, one section of which holds a catheter, the other a lubricant. The package is constructed of inner layers of polyethyene and outer layers of a gas-impermeable metal, e.g. aluminum, foil. The catheter package itself (11) is first gas sterilized with ethylene oxide and then placed within an outer envelope 40, likewise sterilized on the interior. The latter is then sealed.

Stevens U.S. Pat. No. 4,149,635 discloses kits for use in "milogram, arthrogram and angiogram" procedures. The kits provide unfoldable, strip trays in which various instruments needed for medical procedures are arranged sequentially in the package in the order in which the instruments would be needed in the particular procedure. The patentee states that sterilization of the package unit can be accomplished in "conventional ways such as by carbon dioxide or radiation sterilization".

Leigh U.S. Pat. No. 4,153,160 discloses a slide-stop tray kit for use in percutaneous transhepatic cholangiography (PTC) procedures. The kit is composed of an upper tray, the lower side of which slidably engages the upper section of a lower tray. The upper tray contains materials for establishing a sterile field, such as premoistened swabs or surgical drapes, and the lower tray contains instruments and the like which are necessary for the PTC procedure itself. The patentee states that "Prior to shipment, all of the instruments, materials, and both trays are sterilized, e.g. by ethylene oxide sterilization or the like. The sterilized instruments and materials can then be packaged in individual sterile packages . . . which are placed in the appropriate article supporting recesses."

None of these references, and so far as we are aware no other references, address the problem of the packaging of different components of sterile medical procedure packages, which require different means of sterilization for the components, in a single package unit.

BRIEF DESCRIPTION OF THE INVENTION

The package kits provided by the present invention successfully address the problem, not dealt with by the prior art, of providing, in a single sterile package, all the diverse, essential components, including a rubber closured vial of a medicament agent such as a radiopaque agent, required for use in medical procedures.

More specifically, the present invention is directed to medical procedure packages comprising a pre-sterilized unit within an outer package wrap having a sterilized interior, the inner unit comprising an essentially unitary, two-compartment kit pre-sterilized by ethylene oxide and wrapped within an inner package wrap, one compartment of the kit containing essential medical procedure components which are compatible with, and after placement in said compartment are subjected to sterilization by, ethylene oxide, the second compartment of the two-compartment kit containing a rubber closured vial of medicament agent which is incompatible with ethylene oxide sterilization and which is heat sterilized separately before placement in said second compartment of the ethylene oxide sterilized kit.

BRIEF DESCRIPTION OF THE DRAWINGS

The invention is described below with reference to the accompanying drawings wherein:

FIG. 2A is a perspective view of an inner package unit of a second embodiment of the invention, hereinafter designated Configuration 2.

FIG. 3 is a perspective view of a medicament-containing vial which is one of the elements contained within the package kit units of the present invention.

DETAILED DESCRIPTION OF THE INVENTION

The invention will now be described in detail with reference to the foregoing drawings wherein like numerals are used to identify like parts.

Figure 1A:
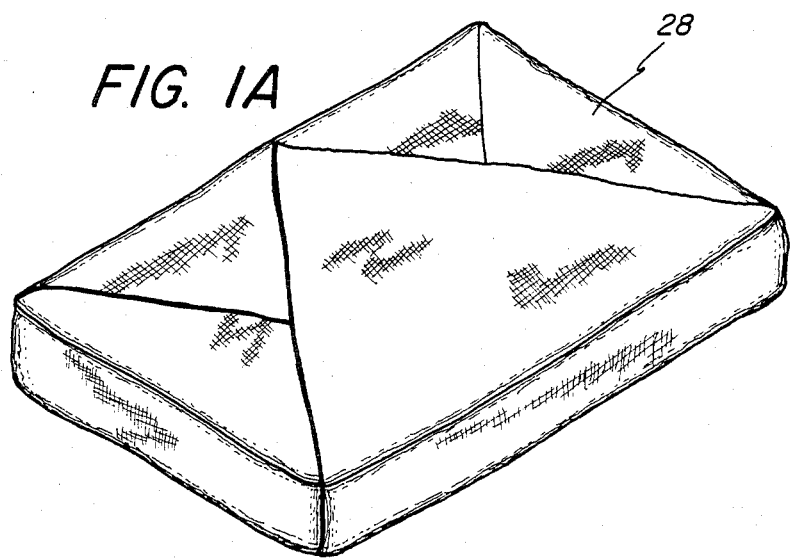
FIG. 1A is a perspective view of a pre-sterilized inner package unit, wrapped in an inner package wrap, as it would appear upon removal from an outer package wrap.
Figure 4:
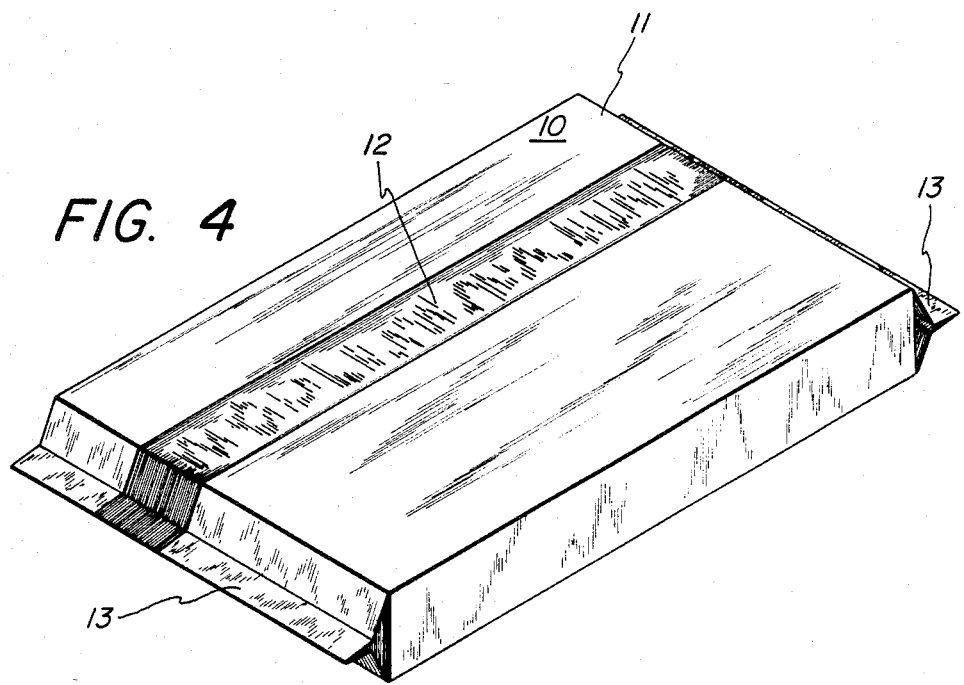
FIG. 4 is a perspective view of the package kit units of Configurations 1 and 2 as they would appear within an outer package wrap and as they would be delivered, through commercial channels, to a doctor, a hospital or a clinic.

As stated before, this invention relates to two configurations of inner pre-sterilized package units which comprise essentially two-compartment kits, said inner pre-sterilized units being shipped in commerce within an outer package wrap, the entire package, represented by general reference numeral 10, being shown in FIG. 4. The outer package wrap 11 consists of a suitable package material, such as plastic or preferably pasteboard, sealed around an inner package unit, to be described below with reference to FIGS. 1A, 1B, 2A and 2B. The ouer wrap may bear printed matter 12 to indicate the nature of the package contents and the commercial origin of the package. The ends of the outer wrap contain flaps 13 which are sealed, for example, by heat or glue sealing.

In the packaging of sterile items, such as the medical procedure units of the present invention, it is required practice that the sterilized items be covered with four layers of a sterile hospital wrap, conventionally of paper. Thus the package units of the present invention, as they would be removed from the outer wrap 11 in Configuration 1 and as they would be removed from an inner envelope 30 packaged within the outer wrap 11 in Configuration 2, would be wrapped within an inner package wrap 28, shown in FIGS. 1A, 1B, 2A and 2B is such a way, to be described below, as to provide the requisite four layers of hospital wrap over the open top of the inner package.

One configuration of the inner package unit, designated Configuration 1, as it would appear when the inner package wrap described above is unfolded, is depicted in FIG. 1B. As shown there, the inner package comprises a set-up tray 14, for example of molded or thermo-formed plastic having essentially two compartments. One compartment 15 is relatively large and is equipped with appropriate dividers or flexible holding means for storing various medical instruments or supplies, such as scrubbing or cleansing means 16 comprising sponge scrubbers with attached handles, local anesthesia producing means 17 comprising a glass vial containing a local anesthetic, local anesthetic syringe injection means 18, local anesthetic syringe needle/sheath/cap 18', sampling or drug transfer means 19 comprising cannulas fitted with male and female tapered joints on either end, drug syringe injection means 20, drug syringe puncture needle/sheath/cap 20', and fluid sampling means 21. The kit may also contain folded patient covering means 22, such as a surgical drape, and swabbing/bandage means 23, such as fiolded gauze pads. In this embodiment, the tray 14 is equipped with a separate, relatively small medicament vial compartment 27.

In the embodiment of Configuration 1, the set-up tray is so-constructed that the compartment 27 is a cavity which is open both from the bottom and the top of the tray. The bottom and top openings of the compartment are sealed by water proof, bacteria proof, sterile, peel-off barrier layers 24, which, on removal, provide access to vial compartment 27 holding vial 26 which is shown in FIG. 3.

Figure 1B:
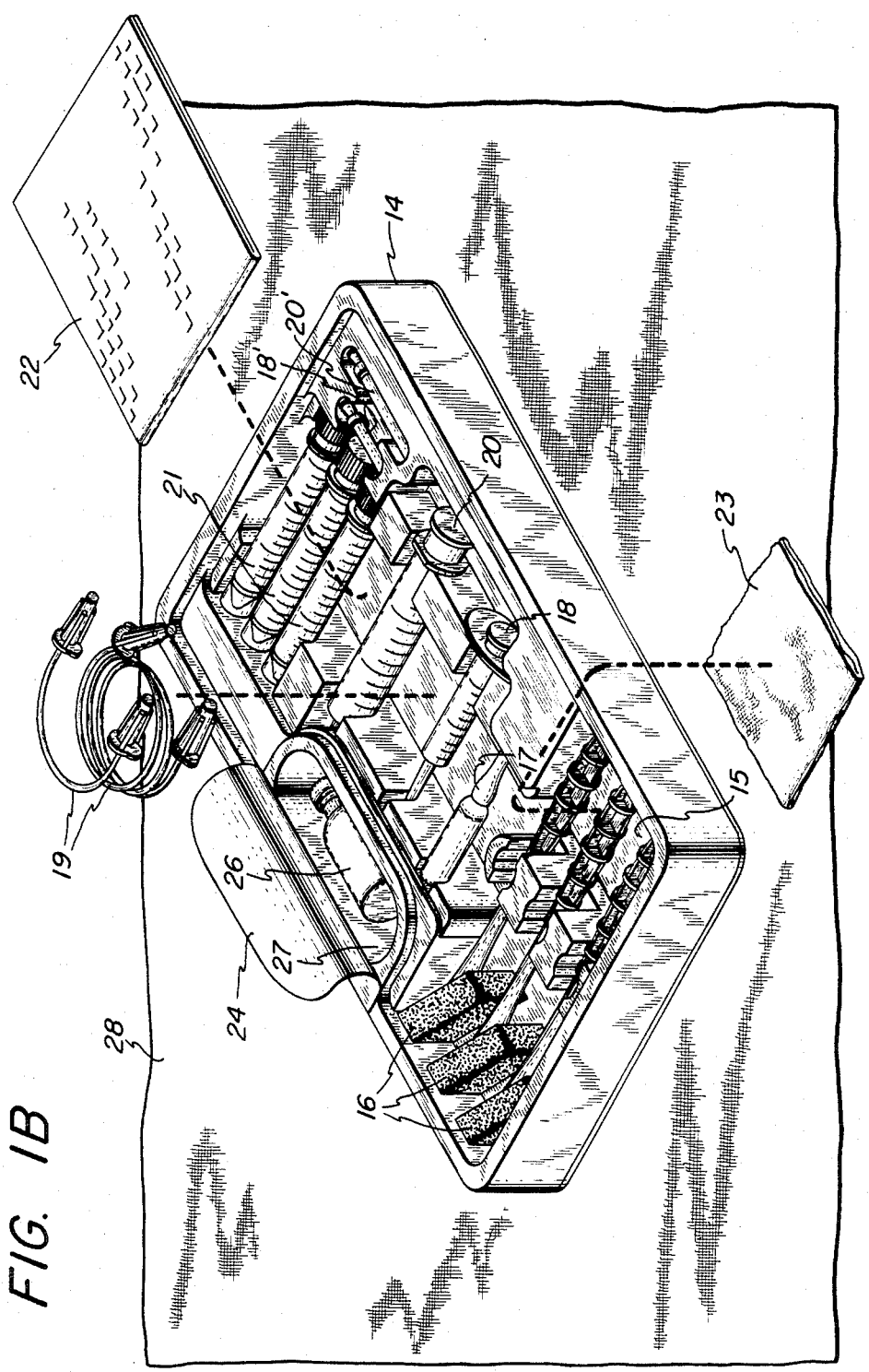
FIG. 1B is a perspective view of an inner package unit of one embodiment of a pre-sterilized package kit of the invention, hereinafter designated Configuration 1, with an inner package wrap unfolded to show an open compartment containing a separately heat sterilized medicament containing vial.

The inner package wrap 28 has a hole at its center generally corresponding in size to the length and width of the tray 14, and the inner wrap is sealed to the back of the set-up tray, so that upon unfolding the inner wrap, as depicted in FIG. 1B, the set-up tray with the compartment 15 containing items 6–23 is exposed, and access is provided to compartment 27 through the top opening thereof.

In preparing the embodiment of Configuration 1 for commercial use, the tray, with all its components 16–23, except vial 26, in place in their respective compartments, wit compartment 27 sealed at both top and bottom by peelable barriers 24 and with the inner wrap 28 sealed to the back of the tray and wrapped around the package, is subjected to ethylene oxide sterilization. The inner package wrap 28 and peelable barrier layers 24 are both permeable to the sterilizing gas, and so all parts of the set-up tray and its compartments, including the interior of vial compartment 27, are sterilized. The package, transferred to a laminar flow, sterile work station, is then inverted, the vial compartment 27 is opened by removal of the peelable barrier sealing the bottom of the compartment, a vial of medicament agent 26, which has been previously heat sterilized elsewhere, is placed in vial compartment 27, and the latter is sealed in compartment 27 with a new, sterile, water proof, bacteria-proof barrier 24. The package is then placed within a sterile outer package wrap 11 which is then sealed at 13.

Figure 2B:
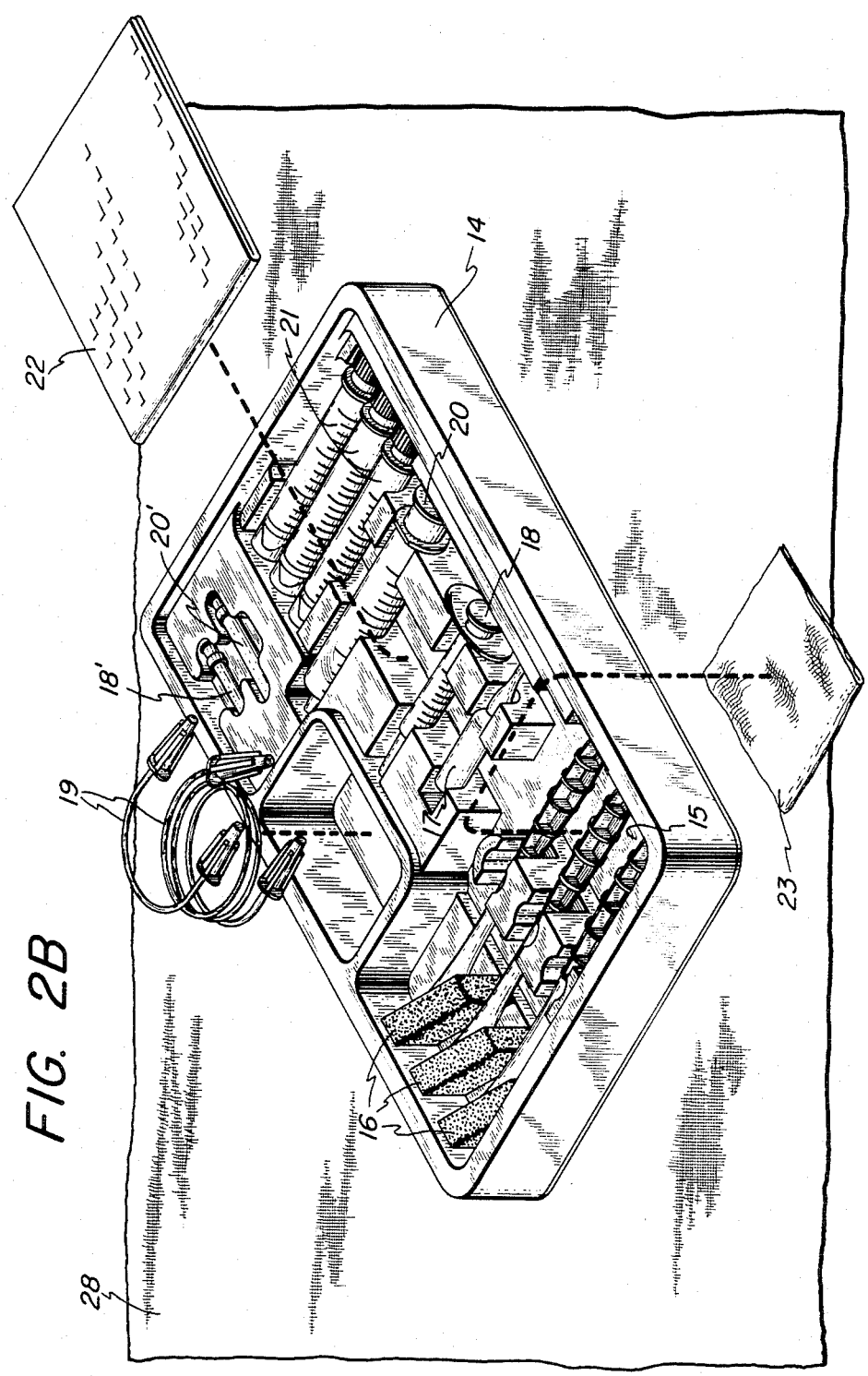
FIG. 2B is a perspective view of a pre-sterilized inner package unit, hereinafter designated Configuration 2, as it would appear when completely unwrapped from within an inner package wrap.

Another embodiment of the inner package of the invention, designated Configuration 2, is depicted in FIGS. 2A and 2B. In this embodiment, the assembled tray, wrapped in an inner package wrap 28, and vial 26, itself wrapped in an outer wrap 28', are sealed, for example by heat sealing, as at 25, within separate compartments 29/29' of an ethylene oxide permeable plastic envelope 30. With the exception that, in this embodiment, the tray 14 does not have a separate compartment for the vial, the tray is similar to the tray used in the embodiment of Configuration 1 and contains all the other items 16–23 carried by the tray in that embodiment. These components, except covering means 22 and swabbing/bandage means 23, are shown in FIG. 2B.

In preparing the embodiment of Configuration 2 for commercial use, the tray is assembled, wrapped and heat sealed in one end of an ethylene oxide permeable plastic envelope. The other end of the envelope is left unsealed, and the envelope, with the assembled and inner wrapped tray 14 inside the large compartment 29 of envelope 30, together with an empty outer package wrap 11, are ethylene oxide sterilized. The sterilized package is then transferred to a clean, laminar flow, sterile work station, and a vial 26, previously heat sterilized elsewhere, and itself wrapped in a sterile inner wrap 28', is inserted in the smaller open compartment 29'. The latter is then heat sealed, the envelope is placed inside a sterile outer package wrap 11, and the flags 13 of the outer package are sealed.

In use, the entire package, whether of Configuration 1 or 2, including the outer package wrap, would be brought into the operating room and the outer package wrap opened. The inner, sterile package unit containing the tray and medicament vial, either wrapped as in Configuration 1 or contained within an envelope 30 as in Configuration 2, would be allowed to slide out of the outer package wrap onto a sterile surface. The inner package would then be opened under sterile conditions to remove the various contents, including the sterile vial.

In the case of the package of Configuration 1, access to all the package components is provided by unfolding the four corners of sterile hospital wrap 28 and peeling back the peelable barrier 24 over the vial compartment 27. The unfolded inner wrap provides a sterile field for placement of each of the tray components as they are removed from the tray.

In the case of the package of Configuration 2, the sterile inner package, consisting of the two-compartment plastic envelope, is opened at either end, for example using scissors, and the contents of both compartments, the vial and the set-up tray, are removed and placed on a sterile surface. As with the embodiment of Configuration 1, unfolding the four corners of the inner wrap 28 from around the tray provides access to all the tray components and also provides a sterile field for placement of each of the components as they are removed from the tray.

It will be seen that when the packages of the invention are prepared and used as described above, the internal sterility of the packages and their contents is maintained from final package sealing until the packages are opened for use.

Although the invention has been described herein with particular reference to the application thereof to myelographic procedures and the various medical procedure components and medicament agent essential thereto, it will be understood that it is contemplated that the inventive concept here-involved can also be applied and adapted to any medical procedure which requires use of components or medicament vials, which are in whole or in part constructed of rubber which thereby require a different method of sterilization, such as heat sterilization, than the other components.

Moreover, although the embodiment of Configuration 2 has been described as employing a plastic envelope having two compartments produced by heat sealing the ends thereof, it is also contemplated that plastic envelopes having a peel-off top wall, which are conventional in the art, would be fully operative in the practice of the invention and are thus considered to be within the purview of the invention.

Having thus described the invention and the advantages thereof, it is considered that the invention is to be broadly construed and limited only by the character of the following claims.

We claim:

1. A medical procedure package comprising in combination:
   A. a sealed, pre-sterilized outer package wrap containing therein:
   B. an essentially unitary, two-compartment kit wrapped within an inner package wrap, the first of said compartments being relatively large and comprising:
      (a) a medical procedure set-up tray and associated essential medical procedure components, said outer package wrap, set-up tray, essential medical procedure components and inner package wrap being sterilized by, and compatible with, ethylene oxide sterilization, and the second of said compartments being relatively small and comprising:
      (b) a space sealed by a bacteria proof peelable barrier layer and holding a medicament containing rubber closured vial, said vial being separately sterilized by, and compatible with, heat sterilization.

2. A medical procedure package according to claim 1 wherein the interior of said outer package wrap and said tray and associated essential medical procedure components are sterilized by ethylene oxide and said peelable barrier seal is added after said vial, sterilized by heat sterilization, is added to saidd second compartment.

3. A medical procedure package according to claim 2 which is adapted for myelographic examination wherein said vial contains a myelographic radiopaque agent.

4. A medical procedure package according to claim 3 wherein said essential medical procedure components comprise scrubbing/cleansing means, local anesthesia producing means, local anesthetic injection means, sample/drug transfer means, drug injection means, fluid sampling means, patient covering means and swabbing/bandage means.

5. A medical procedure package comprising in combination:
   A. a sealed, pre-sterilized outer package wrap containing therein:
   B. an essentially unitary, two-compartment kit comprising a plastic envelope having two heat-sealed compartments, said kit containing in the first of said compartments:
      (a) a medical procedure set-up tray and associated essential medical procedure components, said outer package wrap, set-up tray, essential medical procedure components and inner package wrap being sterilized by, and compatible with, ethylene oxide sterilization, and in the second of said compartments:
      (b) a medicament containing rubber closured vial, said vial being separately sterilized by, and compatible with, heat sterilization, and wherein at least one of said first and second compartment contents (a) and (b) is wrapped within an inner package wrap.

6. A medical procedure package according to claim 5 wherein said envelope containing said tray and its associated essential medial procedure components and said outer package wrap are sterilized by ethylene oxide and said vial is heat sterilized and sealed within said second compartment.

7. A medical procedure package according to claim 6 which is adapted for myelographic examination wherein said vial contains a myelographic radiopaque agent.

8. A medical procedure package according to claim 7 wherein said essential medical procedure components comprise scrubbing/cleansing means, local anesthesia producing means, local anesthetic injection means, sample/drug transfer means, drug injection means, fluid sampling means, patient covering means and swabbing/bandage means.

* * * * *

UNITED STATES PATENT AND TRADEMARK OFFICE
CERTIFICATE OF CORRECTION

PATENT NO. : 4,523,679
DATED : June 18, 1985
INVENTOR(S) : Paikoff et al.

It is certified that error appears in the above-identified patent and that said Letters Patent are hereby corrected as shown below:

Column 1, line 42, change "skin area of" to read -- skin area on --.

Column 2, line 2, change "procedures" to read -- procedure --.

Column 2, line 21, change "in" to read -- is --.

Column 4, line 46, change "ouer" to read -- outer --.

Column 4, line 60, change "is" to read -- in --.

Column 5, line 16, change "fiolded" to read -- folded --.

Column 5, line 33, change "6" to read -- 16 --.

Column 5, line 39, change "wit" to read -- with --.

Column 6, line 16, change "flags" to read -- flaps --.

Column 7, Claim 2, line 34, change "saidd" to read -- said --.

Column 8, Claim 6, line 27, change "medial" to read -- medical --.

Signed and Sealed this

Fifteenth Day of October 1985

[SEAL]

Attest:

DONALD J. QUIGG

Attesting Officer

Commissioner of Patents and
Trademarks—Designate